United States Patent
Ohtsuka et al.

(10) Patent No.: US 8,182,860 B2
(45) Date of Patent: May 22, 2012

(54) DENTAL FILLER

(75) Inventors: Keisuke Ohtsuka, Fukuoka (JP);
Yoshifumi Miyano, Fukuoka (JP);
Hirokazu Tanaka, Kitakyushu (JP);
Eiko Tanaka, legal representative,
Kitakyushu (JP)

(73) Assignee: JGC Catalysts and Chemicals Ltd.,
Kanagawa (JP)

( * ) Notice: Subject to any disclaimer, the term of this patent is extended or adjusted under 35 U.S.C. 154(b) by 516 days.

(21) Appl. No.: 12/225,594

(22) PCT Filed: Mar. 23, 2007

(86) PCT No.: PCT/JP2007/053430
§ 371 (c)(1),
(2), (4) Date: Sep. 25, 2008

(87) PCT Pub. No.: WO2007/111066
PCT Pub. Date: Oct. 4, 2007

(65) Prior Publication Data
US 2009/0253825 A1    Oct. 8, 2009

(30) Foreign Application Priority Data

Mar. 28, 2006 (JP) .................. 2006-086800

(51) Int. Cl.
*A61K 6/083* (2006.01)
(52) U.S. Cl. ....... 427/2.26; 523/114; 523/115; 523/116; 523/117
(58) Field of Classification Search .......... 427/2.26; 523/114–117; *A61K 6/083*
See application file for complete search history.

(56) References Cited

U.S. PATENT DOCUMENTS

| 4,503,169 A | 3/1985 | Rrandkley |
| 5,888,472 A * | 3/1999 | Bem et al. ................. 423/713 |
| 5,891,417 A * | 4/1999 | Bem et al. ................. 423/700 |

(Continued)

FOREIGN PATENT DOCUMENTS

CA    2348066 C  *  7/2010

(Continued)

OTHER PUBLICATIONS

Ferreira, Paula, et al, Synthesis and Structural Characterization of Zirconium Silicates, Chemistry of Materials, 2001, vol. 13, No. 2, pp. 355-363.

Ilyshin, G. D., Hydrothermal Crystallization in the KR-$ZrO_2$-$SiO_2$-$H_2O$ System at 400°C: Phase Equilibria and Modeling of $ZrSiO_4$, $K_2ZrSi_6O_{15}$, $K_2ZrSi_3O_9$, $K_3ZrF_7$, and $ZrO_2$ Crystal Structures, Shubnikov Insitute of Crystallography, 2003, vol. 48, No. 6, pp. 1047-1058.

(Continued)

*Primary Examiner* — James J Seidleck
*Assistant Examiner* — Peter A Salamon
(74) *Attorney, Agent, or Firm* — Leydig, Voit & Mayer, Ltd.

(57) ABSTRACT

The present invention provides dental fillers having the optical and/or mechanical characteristics required to dental materials, a method of producing the same, and a dental composite material prepared with use of the dental filler. More specifically, the present invention provides a dental filler containing a zirconium silicate compound, especially a zirconium trisilicate compound with a wadeite type crystalline structure and having an average particle diameter in the range from 2 to 50,000 nm, a method of producing the same, a dental composite material containing the dental filler and a hardenable resin selected from an acrylic resin, a methacrylic resin, an epoxy resin, a vinyl resin, a urethane resin and the like.

4 Claims, 2 Drawing Sheets

U.S. PATENT DOCUMENTS

| | | | |
|---|---|---|---|
| 6,194,481 B1 * | 2/2001 | Furman et al. | 522/77 |
| 6,232,367 B1 * | 5/2001 | Kobashigawa et al. | 523/116 |
| 6,533,969 B1 * | 3/2003 | Daskalon et al. | 264/16 |
| 2002/0193163 A1 | 12/2002 | Bridges | |
| 2003/0183964 A1 * | 10/2003 | Daskalon et al. | 264/16 |
| 2004/0197738 A1 * | 10/2004 | Ban et al. | 433/202.1 |
| 2004/0224087 A1 * | 11/2004 | Weimer et al. | 427/212 |
| 2005/0127544 A1 * | 6/2005 | Brodkin et al. | 264/16 |
| 2005/0256222 A1 * | 11/2005 | Jones et al. | 523/116 |
| 2006/0004122 A1 | 1/2006 | Hecht et al. | |
| 2006/0116438 A1 * | 6/2006 | Maletz et al. | 523/116 |
| 2010/0317819 A1 * | 12/2010 | De Keyzer et al. | 528/33 |

FOREIGN PATENT DOCUMENTS

| | | |
|---|---|---|
| EP | 1 547 572 | 6/2005 |
| EP | 1923423 A1 * | 5/2008 |
| JP | H07-196428 | 8/1995 |
| WO | WO 0025729 A1 * | 5/2000 |
| WO | WO 01/30304 | 5/2001 |
| WO | WO 01/30305 | 5/2001 |
| WO | WO 01/30306 | 5/2001 |
| WO | WO 0241045 A1 * | 5/2002 |
| WO | WO 02057374 A1 * | 7/2002 |
| WO | WO 2005/115936 | 12/2005 |

OTHER PUBLICATIONS

Ilyshin, G. D., Hydrothermal Crystallization in the KF-Zr02-Si02-H2O System at 400°C: Phase Equilibria and Modeling of ZrSi04, K2Z4Si6015, K2ZrSi309, K3ZrF7, and Zr02 Crystal Structures, Shubnikov Insitute of Crystallography, 2003, vol. 48, No. 6, pp. 1047-1058.

Inorg. Chem. 1997, 36, 3072-2079; Syntheses and X-ray Powder Structures of $K_2(ZrSi_3O_9) \cdot H_2O$ and Its ion-Exchanged Phases with Na and Cs. 1997 American Chemical Society.

Dutch, S., *3-Membered Ring Structures (Benitoite and Wadeite)*, Natural and Applied Sciences, Si3O9 Structure, pp. 1-4, Created Feb. 22, 2001, http://www.uwgb.edu/dutchs/petrolgy/BenitoiteStructure.HTM.

Poojary, D. M., *Syntheses and X-ray Powder Structures of $K_2(ZrSi_3O_9)$-$H_2O$ and Its Ion-Exchanged Phases with Na and Cs*, Inorg. Chem., 36 (14), pgs. 3072-3079, 1997.

Wadeite Mineral Data, Excalibur Mineral Company, pp. 1-4 http://webmineral.com/dataWadeite.shtml, Jan. 24, 2012.

\* cited by examiner

DENTAL FILLER

CROSS-REFERENCE TO RELATED APPLICATIONS

This patent application is a U.S. national phase of International Patent Application No. PCT/JP2007/053430, filed on Feb. 23, 2007.

TECHNICAL FIELD

The present invention relates to a dental filler containing inorganic oxide microparticles with a crystalline structure and a method of producing such dental filler, and also relates to a dental composite material containing the dental filler and a hardenable resin.

BACKGROUND TECHNOLOGY

Recently, in the field of composite materials for dental use, not only a strength and hardness equivalent to those of natural teeth, a surface smoothness, and resistance against abrasion as caused by teething, but also such factors as compatibility in color tone with natural teeth and conformity in a refractive index for providing transparency equivalent to that of natural teeth are required. Furthermore, ordinary materials for dental use are required to have an X-ray radiopacity enabling differentiation of a portion treated or repaired with the materials from a tooth tissue of natural teeth, and in addition the materials are required to have easiness in processing for dentists or dental technicians.

As an example of the composite materials for dental use, for instance, Patent document 1 discloses a composite material for dental use comprising a polymeric resin and non-vitric microparticles (i.e., a mixture of polycrystalline ceramic metal oxide and amorphous silicon oxide) with the X-ray radiopacity. However, because the non-vitric microparticles contain a polycrystalline ceramic metal oxide, it is difficult to obtain the transparency equivalent to that of natural teeth. On the other hand, when the microparticles containing the metal oxide prepared by heating at a temperature of not causing crystallization of the metal oxide are employed for acquiring the transparency, the strength of the microparticles is insufficient, and if the composite material contains such microparticles, the strength and the hardness at the treated or repaired portion of a tooth (including an artificial tooth) are lowered, and sometimes a degree of the resistance against abrasion as caused by teething becomes insufficient.

Patent document 2 discloses a dental filler for producing a composite material, which comprises silicon dioxide and other metal oxide each forming an independent amorphous layers prepared by aggregating particles of silicon dioxide and at least the other metal oxide (e.g., zirconium oxide or the like) and heating them at a temperature of lower than crystallization temperatures of the oxides. However, because the dental filler is prepared by aggregating the particles of silicon dioxide and other metal oxide, the pore volumes of the aggregated particles and also the strength thereof are not adjustable to a desired value. Therefore, it is difficult to improve the transparency at the treated or repaired portion of a tooth (including an artificial tooth). Furthermore, as the adhesion of the aggregated particles to the polymeric resin is insufficient, the strength and the hardness at the treated or repaired portion of a tooth (including an artificial tooth) are lowered, and sometimes a degree of the resistance against abrasion as caused by teething becomes insufficient, like in the case described above.

Furthermore, 3M Innovative Properties Company in the United State made a series of patent applications for materials for dental use (Refer to Patent documents 3 to 5).

Patent document 3 discloses a dental material containing a) a hardenable resin, and b) a filler containing (i) nano size particle cluster containing non-heavy metal oxide particles (such as silica particles) and heavy metal oxide particles (such as zirconium oxide particles), which is not fully densified, and (ii) not-aggregating non-heavy metal oxide nano-sized particles or not-aggregating heavy metal oxide nano-sized particles. The nano-sized particle cluster is substantially amorphous, and is used to improve strength of dental materials, and in addition the nano-sized particles are used for providing beauty, glazing property, and improving the abrasion resistance. When this material is used, however, because the filler has not been fully densified, the compression strength of dental materials using such filler is generally regarded as insufficient, although the tensile strength thereof is improved.

Patent document 4 discloses a dental material containing non-heavy metal oxide particles having the average particle diameter of less than about 300 nm, a heavy metal oxide or heavy metal oxide particles having the average particle diameter of less than about 100 nm, and a hardenable resin. The document includes the descriptions that spherical silica particles or an aggregated material thereof is used as the non-heavy metal oxide particles and that crystalline zirconium oxide particles having a high refractive index and a high X-ray scattering capability or an aggregated material thereof is used as the heavy metal oxide particles. When the material is used, however, because a refractive index of the heavy-metal oxide particles is higher than that of the hardenable resin, a degree of the light scattering inside the material becomes larger and the material may be whitened. As a result, the effect of generating beauty may be rather deteriorated, although the glazing property is improved.

Patent document 5 discloses a dental filler containing substantially amorphous cluster containing non-heavy-metal oxide particles (such as silica particles) having the average particle diameter of less than about 100 nm and heavy-metal oxide particles (such as zirconium oxide particles) having the average particle diameter of less than about 100 nm. In this case, the substantially amorphous cluster is essentially free of crystalline structure. However, because the filler comprises the substantially amorphous cluster, the mechanical strength (especially, the compression strength) of the portion treated or repaired with use of such filler may not be sufficient, although the required mechanical strength varies dependent upon its use or application.

On the other hand, Non-patent document 1 discloses a method of synthesizing a wadeite compound ($K_2ZrSi_3O_9 \cdot H_2O$) by mixing $SiO_2$ (dissolved in KOH solution) with a $Zr(OC_3H_7)$ solution, putting the mixture solution in a stainless steel Teflon™ vessel and then carrying out a reaction between the above components at the temperature of 180° C. for 5 days. In this document, however, only physical properties of the synthesized wadeite compound and the like are described in detail, and there is not even a suggestion that the wadeite compound is applicable or useful as a material for a dental use.

The present inventors devoted themselves to solve the problems in the conventional filler for dental use as described above, and found that zirconium silicate compounds have excellent properties as a dental filler, and completed the present invention.

Patent document 1: JP S60-233007A
Patent document 2: JP H07-196428A

Patent document 3: JP 2003-512404A (WO01/030304)
Patent document 4: JP 2003-512405A (WO01/030305)
Patent document 5: JP 2003-512406A (WO01/030306)
Non-patent document 1: Inorganic Chemistry Vol. 36, No. 14 (1997), Pages 3071-3079

DISCLOSURE OF THE INVENTION

Problems to be Solved by the Inventions

As described above, dental composite materials used in dental treatment are required to have not only such characteristics as nontoxic and insoluble properties, but also strength and hardness equivalent to those of natural teeth, resistance against abrasion as caused by teething, surface smoothness after polishing by a dentist, an appropriate refractive index for providing transparency equivalent to that of natural teeth, glazing property, color tone compatible with that of natural teeth, an X-ray radiopacity ensuring differentiation from natural teeth during or after treatment and the like, and most of the properties largely depend on the physical properties of a dental filler used when a composite material for dental use is produced.

The present invention relates to a novel dental filler capable of satisfying the requirements, and an object of the present invention is to provide a dental filler containing inorganic oxide microparticles which are at least made from a zirconium silicate compound, preferably a zirconium trisilicate compound, and more preferably a zirconium trisilicate compound with a wadeite type crystalline structure, a method of producing the dental filler, and a composite material prepared with use of such filler containing the above inorganic oxide microparticles for dental use.

Means for Solving the Problems

The present invention provides a dental filler containing inorganic oxide microparticles having an average particle diameter in the range from 2 to 50000 nm which are at least made from a zirconium silicate compound.

The zirconium silicate compound is preferably a zirconium trisilicate compound with a wadeite type crystalline structure.

The inorganic oxide microparticles are preferably subjected to surface treatment with one or more organic metal compounds selected from the group consisting of organic silicon compounds, organic titanium compounds, and organic zirconium compounds.

Furthermore, a refractive index of the dental filler is preferably in the range from 1.43 to 1.65.

The present invention also provides a method for producing a dental filler containing inorganic oxide microparticles having an average particle diameter in the range from 2 to 50000 nm which are at least made from a zirconium silicate compound, and the method comprises the steps of:
(a) adding an alkali metal hydroxide and hydrogen peroxide to an aqueous solution containing a hydrate of zirconium oxide and agitating the mixture solution to prepare an aqueous solution in which the hydrate of zirconium oxide is peptized and dissolved;
(b) adjusting the concentration of zirconium components contained in the aqueous solution according to necessity and mixing the aqueous solution with an aqueous solution of silicic acid;
(c) putting the mixture aqueous solution in a reaction vessel to subject it to a hydrothermal treatment at a temperature in the range from 100 to 350° C.;
(d) drying a solid material contained in the mixture aqueous solution; and
(e) calcining the solid material at a temperature in the range from 750 to 1200° C.

The hydrate of zirconium oxide used in the step (a) is preferably prepared by water-washing a neutralized reaction product obtained by adding ammonia or ammonia water to an aqueous solution of one or more zirconates selected from the group consisting of zirconium oxychloride, zirconium oxysulphate, zirconium oxynitrate, zirconium oxyacetate, zirconium oxycarbonate, and ammonium zirconium oxycarbonate. Furthermore, the alkali metal hydroxide used in the step (a) is preferably potassium hydroxide.

The hydrothermal treatment in the step (c) is preferably carried out in an autoclave for 10 to 100 hours.

The drying step in the step (d) is preferably performed by either drying in a hot-air or spray-drying with a spray dryer.

The surface of the solid material is preferably treated by adding one or more organic metal compounds selected from the group consisting of organic silicon compounds, organic titanium compounds, and organic zirconium compounds to a mixture in which the solid material obtained in the process (d) or (e) is dispersed in water and/or an organic solvent to cause the hydrolysis reaction of the organic metal compounds.

The present invention further provides a dental composite material containing the dental filler as described above and a hardenable resin.

The hardenable resin is one or more ones selected from the group consisting of acrylic resin, meta-acrylic resin, epoxide resin, vinyl resin, and urethane resin.

The dental composite material is preferably used for dental restoratives, dental adhesives, dental mill blanks, dental cements, artificial dentures, dental corrective devices, adhesive agents for dental correction, dental casting, and dental coating.

EFFECTS OF THE INVENTION

The dental filler according to the present invention is a novel one containing inorganic oxide microparticles having an average particle diameter in the range from 2 to 50000 nm which are at least made from a zirconium silicate compound, preferably a zirconium trisilicate compound, and more preferably a zirconium trisilicate compound with a wadeite type crystalline structure. The dental filler is characterized in that;

a) The inorganic oxide microparticles are at least made from a zirconium silicate compound, particularly a zirconium trisilicate compound with a particular crystallineline structure, when the microparticles are not subjected to surface treatment by organic metal compounds such as an organic silicon compound, an organic titanium compound and an organic zirconium compound. Especially, the color of the inorganic oxide microparticles mainly made from a zirconium trisilicate compound with a wadeite type crystalline structure is white or lucent white. The inorganic oxide microparticles are crystalline particles containing zirconium as a constituent, and therefore have the enough X-ray radiopacity.

b) The inorganic oxide microparticles are superior in mechanical strength and abrasion resistance, and have the density in the range from 2.9 to 3.4 and the hardness (Mohs' scale) in the range from 5.0 to 6.0, when the microparticles are not subjected to the surface treatment. However, even when the surface of the particles are treated with an organic metal compound such as an organic silicon compound, an organic titanium compound and an organic zirconium compound, almost the same effects can be expected.

c) The inorganic oxide microparticles without being subjected to the surface treatment have the refractive index in the range from 1.5 to 1.7, more particularly in the range from 1.55 to 1.64, the index of which is appropriate for a dental use. The refractive index of the particles can be adjusted in the range from 1.43 to 1.65 by surface treatment with the organic metal compound, when adjustment of the refractive index is needed. As a result, the inorganic oxide microparticles, which have an appropriate refractive index for being mixed in a hardenable resin, can be easily obtained.

d) The inorganic oxide microparticles can be used as it is for preparing dental composite materials, although surface treatment may be required dependent upon the kind of hardenable resins to be used. The inorganic oxide microparticles made from a zirconium silicate compound are crystalline, and the surface thereof is chemically inactive, and the dispersibility in a hardenable resin is high, which enables to realize filling with high-density. However, when further higher dispersibility in and adhesion to the hardenable resin is needed, these properties can be improved by surface treatment with the organic metal compound.

e) Since the inorganic oxide microparticles made from a zirconium silicate compound have a very stable crystalline structure and do not contain any poisonous heavy-metal ingredient, the particles are never soluble in saliva or any liquids drunk from a mouth when used as a dental material and give no negative affects on a human body.

The method of producing a dental filler according to the present invention is novel in the points that the method makes it possible to easily synthesize a zirconium silicate compound having high purity, especially the zirconium trisilicate compound with a wadeite type crystalline structure at a high yield, and also that the method does not require, for synthesis of the zirconium silicate compound, such a long time (5 days) as that described in Non-patent document 1.

Furthermore, the dental filler contained in the dental composite material according to the present invention has the optical characteristics and also the mechanical characteristics required for the materials in this field as described above, so that the dental composite material is quite useful as various types of materials used in the current or future dental treatment.

BEST MODE FOR CARRYING OUT THE INVENTION

A dental filler, a method of producing the dental filler, and a dental composite material containing such dental filler each according to the present invention are described in detail below.

[Dental Filler and Method of Producing the Same]
Dental Filler

The dental filler according to the present invention contains inorganic oxide microparticles having an average particle diameter in the range from 2 to 50000 nm, which are at least made from a zirconium silicate compound.

The zirconium silicate compound is preferably a zirconium trisilicate compound with a wadeite type crystalline structure (sometimes referred to simply as "wadeite compound" hereinafter), but may be other types of zirconium silicate compounds expressed by the chemical formulae such as $M_2ZrSi_3O_9$ or $M_2ZrSi_2O_7$ (wherein M represents an alkali metal), or a mixture thereof.

As generally known, the wadeite is a natural stone (a scarce mineral) found in Kola Peninsula in Russia or Western Australia State in Australia. The main component is expressed by the chemical formula of $K_2ZrSi_3O_9$ or $K_2ZrSi_3O_9 \cdot H_2O$, and the crystalline structure is specific and is categorized as the hexagonal system.

Although the inorganic oxide microparticles used as the dental filler according to the present invention are artificially synthesized, the chemical composition and the crystalline structure are identical or close to those of the natural stone. Namely the compounds are crystalline materials comprising the wadeite compound expressed by the chemical formula of $K_2ZrSi_3O_9$ or $K_2ZrSi_3O_9 \cdot H_2O$, a zirconium trisilicate compound expressed by the chemical formula of $Na_2ZrSi_3O_9$, $Na_2ZrSi_3O_9 \cdot H_2O$, $K_xNa_yZrSi_3O_9$, $K_xNa_yZrSi_3O_9 \cdot H_2O$ or the like (wherein x+y=2), a zirconium disilicate compound expressed by the chemical formula of the chemical formula of $K_2ZrSi_2O_7$, $K_2ZrSi_2O_7 \cdot H_2O$, $Na_2ZrSi_2O_7$, $Na_2ZrSi_2O_7 \cdot H_2O$, $K_xNa_yZrSi_2O_7$, $K_xNa_yZrSi_2O_7 \cdot H_2O$ or the like (wherein x+y=2), or a mixture thereof. Of these materials, the inorganic oxide microparticles made from the wadeite compound expressed by the chemical formula of $K_2ZrSi_3O_9$ is preferably used in the present invention.

The inorganic oxide microparticles having the chemical composition and the crystalline structure as described above preferably have the particle density in the range from 2.9 to 3.4, the hardness (Mohs' scale) in the range from 5.0 to 6.0, the refractive index in the range from 1.5 to 1.7 and more preferably in the range from 1.55 to 1.64, and the physical properties are equivalent or close to those of nature-originated zirconium silicate compounds, especially the wadeite compound.

As described above, the inorganic oxide microparticles are at least made from a zirconium silicate compound as described above, but may contain other compounds such as zirconium oxide or silica according to conditions for production thereof. However, when the microparticles are used as the dental filler according to the present invention, there is not any specific restriction over a content of the compounds other than the zirconium silicate compound, but the content is 40% by weight or below, preferably 20% by weight or below, and more preferably 10% by weight or below in the inorganic oxide microparticles.

When the inorganic oxide microparticles are used as a dental filler, it is preferable to use only the inorganic oxide microparticles, but it is allowable to be mixed with other microparticles generally used as dental fillers, for instance, inorganic oxide microparticles such as microparticles of silica or those of zirconium oxide. There is not specific restriction over a quantity of other microparticles (such as silica particles or zirconium oxide particles) mixed with the inorganic oxide microparticles, but the content is 70% by weight or below, preferably 50% by weight, and more preferably 30% by weight in the dental filler. The requirement is also applicable to inorganic oxide microparticles subjected to the surface treatment as described below.

Furthermore, the inorganic oxide microparticles may be subjected, before use, to surface treatment with one or more organic metal compounds selected from the group consisting of an organic silicon compound, an organic titanium compound, and an organic zirconium compound. When subjected to the surface treatment, the inorganic oxide microparticles having a refractive index equivalent to that of a hardenable resin to be mixed with the particles in use can easily be obtained, and the dispersibility in and adhesion to the hardenable resin can be improved.

The organic silicon compound includes, but not limited to, the silicon compound expressed by the following general formula (I):

$$R_n SiX_{4-n} \quad (1)$$

(wherein R represents an unsubstituted or substituted hydrocarbon group containing 1 to 10 carbon atoms, and the hydrocarbon groups may be identical or different from each other. X represents an alkoxy group having 1 to 4 carbon atoms, a silanol group, a halogen group, or hydrogen, and n is an integral number from 0 to 3).

More specifically, the organic silicon compound includes, but not limited to, methyl trimethoxysilane, dimethyl dimethoxysilane, phenyl trimethoxysilane, diphenyl dimethoxysilane, methyl triethoxysilane, dimethyl diethoxysilane, phenyl triethoxysilane, diphenyl diethoxysilane, isobutyl trimethoxysilane, vinyl trimethoxysilane, vinyl triethoxysilane, vinyl-tris(β methoxyethoxy)silane, 3,3,3-trifluoropropyl trimethoxysilane, methyl-3,3,3-trifluoropropyl dimethoxysilane, β-(3,4 epoxycyclohexyl)ethyl trimethoxysilane, γ-glycidoxytripropyl trimethoxysilane, γ-glycidoxypropylmethyl diethoxysilane, γ-glycidoxypropyl triethoxysilane, γ-methacryloxypropylmethyl dimethoxysilane, γ-methacryloxypropyl trimethoxysilane, γ-methacryloxypropylmethyl diethoxysilane, γ-methacryloxypropyl triethoxysilane, N-β(aminoethyl)γ-aminopropylmethyl dimethoxysilane, N-β(aminoethyl)γ-aminopropyl trimethoxysilane, N-β(aminoethyl)γ-aminopropyl triethoxysilane, γ-aminopropyl trimethoxysilane, γ-aminopropyl triethoxysilane, N-phenyl-γ-aminopropyl trimethoxysilane, γ-mercaptopropyl trimethoxysilane, trimethylsilanol, methyl trichloroxysilane, methyl dichloroxysilane, dimethyl dichlorosilane, trimethyl chlorosilane, phenyl trichlorosilane, diphenyl dichlorosilane, vinyl trichlorosilane, trimethyl bromosilane, and diethylsilane. Of these materials, it is preferable to use vinyl trimethoxysilane, vinyl triethoxysilane, γ-methacryloxypropylmethyl dimethoxysilane, γ-methacryloxypropyl trimethoxysilane, γ-methacryloxypropyl methyl diethoxysilane, or γ-methacryloxypropyl triethoxysilane, which are often used as a silane coupling agent, and a mixture thereof.

The organic titanium compound includes, but not limited to, tetramethyl titanate, tetraisopropyl titanate, tetra n-butyl titanate, butyl titanate dimmer, and tetra (2-ethylhexyl)titanate. The organic zirconium compound includes, but not limited to, zirconium isopropoxide, zirconium n-butoxide, zirconium acetylacetonate, and zirconyl acetate.

Furthermore, if required, the surface treatment may be carried out with an organic aluminum compound such as aluminum acetyl acetonate, and chilate compound of organic salt of aluminum.

The surface treatment with the organic metal compound may be performed with a mixture of the organic metal compounds, and furthermore may be carried several times with the same organic metal compound, or with different types of organic metal compounds.

A thickness of the organic metal oxide (or a hydrolyte thereof in a case of an organic silicon compound containing silane, an organic titanium compound, or an organic zirconium compound) bonded to or covering a surface of the inorganic oxide microparticles is 300 nm or below, and preferably 100 nm or below, although the thickness varies dependent upon a type of the organic metal compound used in the surface treatment, or a desired value to a refractive index, dispersibility or other property of the inorganic oxide microparticles to be obtained. If the thickness is over 300 nm, some of the organic metal compound not fully hydrolyzed during the surface treatment and having the hydrosis group remained, and/or some of the products reacted between the metal compounds themselves without having reacted with or adhered to the surfaces of the microparticles may exist in the layer formed on the surfaces of the microparticles, thereby the stability of the particle surface being degraded with a time elapse, and when such microparticles are dispersed in a hardenable resin, the microparticles may adhere to each other or may aggregate, which is not preferable.

A refractive index of the inorganic oxide microparticles obtained as described above is in the range from 1.43 to 1.65, preferably in the range from 1.45 to 1.60, although the value varies on whether the microparticles are subjected to the surface treatment or dependent upon a type of the organic metal compound used in the surface treatment or a thickness achieved through the surface treatment. If the refractive index is less than 1.43, because the value is lower than a refractive index of the hardenable resin, a degree of light scattering inside the microparticles increases, and as it makes a cause of whitening, the desired beauty would not be obtained. If the refractive index is over 1.65, because the value is higher than a refractive index of the hardenable resin, a degree of light scattering inside the microparticles increases also in this case, and as it makes a cause of whitening, the desired beauty would not be obtained.

Whether or not the surface treatment is performed, it is preferable to use the inorganic oxide microparticles having an average particle diameter in the range from 2 to 50000 nm, preferably in the range from 7 to 5000 nm, and more preferably in the range from 10 to 500 nm. If the average particle diameter is less than 2 nm, a mechanical strength, especially a compression strength or a bending strength of the dental filler containing the microparticles as described above becomes lower. If the average particle diameter is over 50000 nm, sometime it becomes difficult to polish a treated or repaired portion of a tooth obtained by hardening a dental composite material prepared with the dental filler, and if the treated or repaired portion is polished by a dentist, the surface thereof would not have a sufficient smoothness or glazing property as described above, which is not preferable. In addition, if the inorganic oxide microparticles with a hardness of the particles being relatively high are used, it becomes more difficult to polish the treated or repaired portion as the particle diameter becomes larger.

A method of producing the dental filler according to the present invention is described below, but it is to be noted that the dental filler according to the present invention is not limited to the inorganic oxide microparticles obtained by this method, and microparticles obtained from the natural stones or those produced by other synthesis method based on the conventional or new technology may be used so long as the material includes a zirconium silicate compound, especially a wadeite compound.

Method of Producing a Dental Filler

The method of producing a dental filler according to the present invention is employed for producing a dental filler containing inorganic oxide microparticles having an average particle diameter in the range from 2 to 50000 nm which are at least made from a zirconium silicate compound, and the method comprises the steps of:

(a) adding an alkali metal hydroxide and hydrogen peroxide to an aqueous solution containing a hydrate of zirconium oxide and agitating the mixture solution to prepare an aqueous solution in which the hydrate of zirconium oxide is peptized and dissolved, (b) adjusting the concentration of zirconium components contained in the aqueous solution according to necessity and mixing the aqueous solution with an aqueous solution of silicic acid, (c) putting the mixture aqueous solution in a reaction vessel to subject it to a hydrothermal treatment at a temperature in the range from 100 to 350° C., (d) drying a solid material contained in the mixture aqueous solution, and (e) calcining the solid material at a temperature in the range from 750 to 1200° C.

Each of the steps is described in detail below.

Step (a)

The hydrate of zirconium oxide (sometimes referred to simply as "the zirconium oxide hydrate" hereinafter) in the present invention is expressed by the chemical formula of $ZrO_2.xH_2O$, and also zirconium hydroxide ($Zr(OH)_n$) is included in the category of the zirconium oxide hydrate.

It is generally known that the hydrate of zirconium oxide is dissolved in an acid or in an aqueous solution containing an acid, but is little dissolved in an aqueous solution containing water or alkali.

Therefore, in step (a), a suspended aqueous solution is prepared by suspending zirconium hydroxide in pure water or distilled water. Then, a hydroxide of an alkali metal such as potassium and sodium (namely potassium hydroxide, sodium hydroxide and the like) and hydrogen peroxide are added to the suspended aqueous solution as described above with agitation, thereby the zirconium hydroxide being hydrated, and thus obtained hydrate of zirconium oxide is peptized and dissolved in the mixture solution. When the inorganic oxide microparticles containing the wadeite compound (i.e., $K_2ZrSi_3O_9$ or $K_2ZrSi_3O_9.H_2O$) according to the present invention is produced, potassium hydroxide is used as the hydroxide of an alkali metal.

The alkali metal hydroxide ($M_2O$) is preferably added into the suspended aqueous solution at the molar ratio ($M_2O/ZrO_2.xH_2O$) against the hydrate of zirconium oxide ($ZrO_2.xH_2O$) in the range from 1/5 to 1/1, and preferably in the range from 1/2 to 4/5. When the molar ratio is less than 1/5, peptization of the zirconium oxide hydrate does not proceed well. When the molar ratio is over 1/1, because a percentage of the alkali metal is large, it becomes difficult to obtain a crystalline product of a zirconium silicate compound such as the wadeite compound.

The hydrogen peroxide ($H_2O_2$) is added into the suspended aqueous solution preferably at the molar ratio ($H_2O_2/ZrO_2.xH_2O$) against the zirconium oxide hydrate ($ZrO_2.xH_2O$) in the range from 1/1 to 6/1, and preferably in the range from 12/5 to 4/1. When the molar ratio is less than 1/1, peptization of the zirconium oxide hydrate does not proceed well. When the molar ratio is over 6/1, the peptization proceeds quickly and a time required for dissolution becomes shorter, but a large amount of hydrogen peroxide not reacted yet remains in the aqueous solution, which is not preferable from the economical point of view.

Further, the hydrogen peroxide is preferably added as a hydrogen peroxide solution with the concentration in the range from 18 to 35% by weight.

It is to be noted that the hydrate of zirconium oxide can be prepared by a known conventional method, for instance, by hydrolyzing a zirconium salt in an aqueous solution, or by adding an alkali or ammonia in the aqueous solution to cause a neutralization reaction. In the present invention, however, it is preferable to use a neutralized reaction product (i.e., a hydrate of zirconium oxide) obtained by adding, with agitation, ammonia or ammonia solution into an aqueous solution in which one or more zirconates selected from the group consisting of zirconium oxychloride ($ZrOCl_2.xH_2O$), zirconium oxysulfate ($ZrOSO_4.xH_2O$), zirconium oxynitrate ($ZrO(NO_3)_2.xH_2O$), zirconium oxyacetate ($ZrO(C_2H_3O_2)_2$), zirconium oxycarbonate ($ZrOCO_3.xH_2O$) and ammonium zirconium oxycarbonate (($NH_4)_2ZrO(CO_3)_2$) are dissolved in pure water or distilled water, to cause a neutralization reaction, and then washing thus obtained product by pure water or distilled water sufficiently.

As the zirconate, it is preferable to use zirconium oxychloride ($ZrOCl_2.8H_2O$). It is to be noted that the zirconium oxychloride, the zirconium oxysulfate, the zirconium oxynitrate, the zirconium oxyacetate, and the zirconium oxycarbonate as described above are sometimes also referred to as zirconyl chlorate, zirconyl sulfate, zirconyl nitrate, zirconyl acetate, and zirconyl carbonate respectively.

Furthermore, in place of the zirconate, it is possible to use one or more zirconates selected from the group consisting of zirconium carbonate ($ZrCO_4.ZrO_2.xH_2O$), zirconium sulfate ($Zr(SO_4)_2.xH_2O$), zirconium chloride ($ZrCl_2$, $ZrCl_3$, or $ZrCl_4$), and zirconium nitrate ($Zr(NO_3)_4.xH_2O$).

A content of the above zirconate in the aqueous solution is in the range from 30 to 40% by weight, and preferably in the range from 35 to 37% by weight.

It is preferable to add the ammonia ($NH_3$) or ammonia water ($NH_4OH$) into the aqueous solution at the molar ratio ($NH_3/ZrOX_n$ or $NH_4OH/ZrOX_n$) against the zirconate ($ZrOX_n$) in the range from 13/7 to 13/2, and preferably in the range from 13/5 to 13/4. When the molar ratio is less than 13/7, the zirconate is not neutralized sufficiently, thereby a part of the zirconate being remained in the aqueous solution. When the molar ratio is over 13/2, an amount of ammonia is excessive, and a long time is required for washing off the residual ammonia, which is not preferable.

Furthermore, the ammonia solution is preferably added as an ammonia water with a concentration in the range from 5 to 15% by weight.

The neutralization reaction is preferably performed at a temperature in the range from 5 to 20° C., and more preferably in the range from 10 to 15° C. When the temperature is over 20° C., zirconium compounds other than the zirconium oxide hydrate as byproducts would be produced by neutralization of the zirconate, which is not preferable.

It is necessary to sufficiently wash the hydrate of zirconium oxide obtained from the neutralization reaction and then separated by filtration with pure water or distilled water for removing unreacted materials (such as $ZrOX_n$ or the like) or byproducts ($NH_4X$ and the like) from the neutralization reaction as much as possible.

A content of zirconium components (a peptized product of the zirconium oxide hydrate) dissolved and contained in the mixture aqueous solution obtained as described above is desirably in the range from 8 to 12% by weight in terms of $ZrO_2$, although there is not specific restriction over the value.

Step (b)

In step (b), after a concentration of the zirconium components contained in the mixture aqueous solution obtained in step (a) above is adjusted according to the necessity, the mixture aqueous solution and an aqueous solution of silicic acid are mixed with each other.

A content of the zirconium components contained in the mixture aqueous solution is preferably adjusted to the range from 0.5 to 10% by weight, and more preferably to the range from 1 to 5% by weight in terms of $ZrO_2$, although the value varies dependent upon the properties of the aqueous solution of silicic acid or the concentration of silicic acid to be mixed in this step. When the content is less than 0.5% by weight, a yield of a zirconium silicate compound per unit volume of the mixture aqueous solution becomes smaller, which is not preferable from the economical point of view. When the content is over 10% by weight, stability of the mixture aqueous solution is deteriorated, and in addition viscosity of the mixture aqueous solution is apt to increase, which is also not preferable.

The aqueous solution of silicic acid (sometimes referred to simply as "the aqueous silicic acid solution" hereinafter), which is used in this step, is preferably prepared by treating an aqueous solution of a silicate such as an alkali metal silicate, or an organic base silicate with a cation exchange resin added in the solution, the exchange resin of which is removed thereafter. The silicates include, but not limited to, alkali metal silicates such as sodium silicate (water glass), and potassium silicate and organic base silicates such as a quaternary ammonium silicate.

It is preferable to use the aqueous solution of silicic acid with a pH in the range from 2 to 4, more preferably in the range from 2 to 3, and also with a content of silicon components in the range from 0.1 to 6% by weight, and more preferably in the range from 3 to 4% by weight in terms of $SiO_2$.

When the silicon components contained in the aqueous solution of silicic acid is expressed as $SiO_2$ (i.e., in terms of $SiO_2$) and the zirconium components contained in the mixture aqueous solution is expressed as $ZrO_2$ (i.e., in terms of $ZrO_2$), the aqueous silicic acid solution is preferably mixed with the mixture aqueous solution above at the molar ratio ($SiO_2/ZrO_2$) in the range from 40/30 to 80/10, preferably in the range from 20/10 to 60/10, and more preferably in the range from 30/10 to 72/14. When the molar ratio is less than 40/30, even in the case of having carried out a series of steps of the method according to the present invention, it is difficult to form a crystalline product comprising a zirconium silicate compound, and a crystalline product of zirconium oxide will be formed. When the molar ratio is over 80/10, it becomes difficult to form a crystalline product comprising a zirconium silicate compound.

To describe further precisely, when the molar ratio is in the range from 20/10 to 60/10, mainly a zirconium trisilicate compound and/or a zirconium disilicate compound is formed, and when the molar ratio is in the range from 30/10 to 72/14, a zirconium trisilicate compound such as the wadeite compound is formed. Therefore, it is desirable to carefully select the molar ratio according to a type of usage of the inorganic oxide microparticles finally obtained, namely depending on its use or application for a dental composite material.

Step (c)

In this step (c), the mixture aqueous solution obtained in step (b) is put in a reactor vessel, and is subjected to a hydrothermal treatment at a temperature in the range from 100 to 350° C.

There is no specific restriction over the reaction vessel so long as the vessel is a pressure-resistance and heat-insulating vessel capable of enduring a pressure in the range from 0.5 to 16.5 MPa, but generally it is preferable to use an autoclave made from stainless steel.

The hydrothermal treatment is preferably executed at a temperature in the range from 100 to 350° C. and more preferably in the range from 150 to 200° C. for 10 to 100 hours, preferably for 16 to 70 hours, and more preferably for 20 to 40 hours. When the temperature employed in the hydrothermal treatment is less than 100° C., the reactions between the zirconium components contained in the mixture aqueous solution and the silicon components contained in the aqueous solution of silicic acid do not proceed smoothly, and sometimes it becomes difficult to obtain a zirconium silicate compound, especially a precursor composition (solid material) of the wadeite compound. When the temperature employed in the hydrothermal treatment is over 350° C., a pressure-resistant and heat-insulating vessel capable of enduring the pressure of 16.5 Mpa or more is required, which is not economical from the viewpoint of energy consumption.

When the time for the hydrothermal treatment is less than 10 hours, the reactions between the zirconium components contained in the mixture aqueous solution and the silicon components contained in the aqueous solution of silicic acid do not proceed sufficiently, and sometimes it becomes difficult to obtain a zirconium silicate compound, especially a precursor composition (solid material) of the wadeite compound. Even when the time for the hydrothermal process is over 100 hours, any substantially positive effect is not given for forming the zirconium silicate compound, especially the precursor composition of the wadeite compound, and therefore it is not meaningless to spend the time over 100 hours in this hydrothermal treatment.

Step (d)

In step (d), the solid material contained in the mixture aqueous solution obtained in step (c) is dried.

The solid material contained in the mixture aqueous solution can be dried by any known drying process, for instance, by separating the solid material by filtration, washing the solid material by pure water or distilled water according to the necessity, and then drying the solid material at a temperature in the range from 100 to 200° C.

However, to obtain inorganic oxide microparticles having the particle diameters being not widely ranged and with a narrow particle distribution, it is preferable to adjust a concentration of the solid material contained in the mixture aqueous solution to the range from 0.01 to 10% by weight, preferably to the range from 0.07 to 5% by weight, and more preferably to the range from 0.1 to 3.0% by weight and then spray-dry the solid material with a spray drier. When the solid material concentration is less than 0.01% by weight, a percentage of microparticles with a particle diameter of 10 nm or below increases, which disadvantageously leads to drop of a production yield. When the solid material concentration is over 10% by weight, viscosity of the mixture aqueous solution becomes higher with a degradation of its stability, so that it becomes difficult to obtain inorganic oxide microparticles having the particle diameters being not widely ranged and with a narrow particle distribution. Furthermore, a percentage of particles with a particle diameter of 10000 nm or more increases, and sometimes large-size particles with a particle diameter of more than 50000 nm may be formed. When the large-size particles are used as a dental filler as they are, it becomes difficult to polish a treated or repaired portion of a tooth by a dentist, or the transparency at the treated or repaired portion may become lower.

Any known spray drier (such as the disk rotation type or the nozzle type) may be used as the spray drier. Furthermore, the spray-drying is performed by any known method, namely by spraying the mixture aqueous solution or its concentrated one into a hot air flow.

In this step, a temperature of the hot air stream at the inlet for spraying the mixture aqueous solution is in the range from 150 to 200° C., and preferably in the range from 170 to 180° C. A temperature of the air stream at the outlet thereof is preferably in the range from 40 to 60° C. When the air temperature at the inlet is less than 150° C., the solid material contained in the sprayed mists would not be dried sufficiently. When the air temperature at the inlet is over 200° C., it is not economical. When the air temperature at the outlet is less than 40° C., the solid material contained in the sprayed mists would not be dried sufficiently and sometimes it will adhere to portions inside the spray drier, which is not preferable.

The inorganic oxide microparticles consisting of the sprayed and dried particles obtained as described above have the particle diameters being not widely ranged. With the method, it is also possible to easily obtain inorganic oxide microparticles having an average particle diameter in the range from 10 to 10000 nm.

It is needless to say, however, that the solid material contained in the mixture aqueous solution can be dried in any generally known drying device at a temperature in the range from 100 to 200° C. In this case, however, because it is impossible to obtain inorganic oxide microparticles having the particle diameters being not widely ranged and sometimes a block of the particles is formed, it is necessary to adjust the particle diameters by subjecting the dried particles to a pulverizer or grinder such as a mortar and a bowl mill.

Step (e)

In step (e), the dried particles obtained in step (d) are subjected to calcination at a temperature in the range from 750 to 1200° C.

The dried particles as described above is put in a quartz-made crucible, and is calcined in an electric furnace for 1 hour or more, and more preferably for 3 to 4 hours at a temperature in the range from 750 to 1200° C., more preferably in the range from 1000 to 1100° C. When the temperature employed for the calcination is less than 750° C., it is impossible to obtain a crystalline product comprising a zirconium silicate compound, especially the wadeite compound, and consequently, when the thus obtained product is measured with an X-ray diffractometer, any X-ray diffraction peak indicating presence of the wadeite type crystalline structure does not appear. Furthermore, when the temperature for calcination is over 1200° C., the particles put in the crucible will be sintered, and any desired inorganic oxide microparticles would not be obtained. Furthermore, when the time for the calcination is less than 1 hour, it becomes difficult to obtain a crystalline product comprising a zirconium silicate compound, especially the wadeite compound.

The inorganic oxide microparticles made from the zirconium silicate compound according to the present invention can easily be obtained as described above. However, when particle diameters of the inorganic oxide microparticles (i.e., calcined particles) obtained as described above are larger than a desired value, it is needless to say that the particles may be put in pulverizer or grinder such as a mortar and a bowl mill, to adjust the average diameter to a desired value in the range from 2 to 50000 nm, preferably from 10 to 10000 nm. Thus obtained inorganic oxide microparticles are fully usable or applicable as a filler material for dental use.

When potassium hydroxide is used as the alkali metal hydroxide in step (a), it is possible to easily obtain the inorganic oxide microparticles made from the zirconium trisilicate compound with a wadeite type crystalline structure, namely the wadeite compound ($K_2ZrSi_3O_9$).

Surface Treatment Step

The inorganic oxide microparticles obtained in step (e) have the physical properties as described above, and can be used as the dental filler according to the present invention as they are, although the circumstances may be different in some situations.

When a refractive index of the inorganic oxide microparticles must be adjusted according to that of a hardenable resin which is mixed with the inorganic oxide microparticles, or when dispersibility of the inorganic oxide microparticles in and adhesion thereof to the hardenable resin is to be improved, it is desirable to subject the inorganic oxide microparticles to surface treatment (for improvement of the surface) with one or more organic metal compounds selected from the group consisting of organic silicon compounds, organic titanium compounds and organic zirconium compounds.

There is no specific restriction over a surface treatment method employed in the present invention, but the following method may be employed. Of these methods, the surface treatment methods (2) and (3), especially the surface treatment (3) described below should preferably be used. It is to be noted that any known surface treatment method may be employed for carrying out the present invention.

(1) A method in which an aqueous solution containing the solid material obtained in step (c) is concentrated according to the necessity, then one or more organic metal compounds selected from the group consisting of organic silicon compounds, organic titanium compounds and organic zirconium compounds are added into the aqueous solution to cause a hydrolysis reaction of the organic metal compound for treating the surface of the solid material, and then the solid material is dried. It is necessary, however, to subject the inorganic oxide microparticles obtained by this method to the drying step and the calcining step, and therefore, although the refractive index can be adjusted, improvement in the dispersibility of the inorganic oxide microparticles in a hardenable resin or adhesion thereof to the resin can not be expected so much. Furthermore, when the inorganic oxide microparticles obtained through the drying step are to be subjected to pulverization for adjusting the average particle diameter thereof, some of the particles may be broken into pieces and the surface-treated portion may be lost or dropped off during the pulverization, which spoils the original purpose of the surface treatment.

(2) A method in which the inorganic oxide microparticles (i.e., dried particles) obtained in step (d) are dispersed in water and/or an organic solvent to prepare a mixture solution, one or more organic metal compounds selected from the group consisting of organic silicon compounds, organic titanium compounds and organic zirconium compounds are added into the dispersed solution to cause a hydrolysis reaction of the organic metal compounds for treating the surface of the inorganic oxide microparticles, and then the inorganic oxide microparticles are dried. In this method, however, the inorganic oxide microparticles obtained by this method are required to subject the calcining step. Therefore, although the refractive index can be adjusted, improvement in dispersibility of the inorganic oxide microparticles in a hardenable resin or adhesion to the resin can not be expected so much.

(3) A method in which the inorganic oxide microparticles (i.e., calcined particles) obtained in step (e) are dispersed in water and/or an organic solvent to prepare a mixture solution, one or more organic metal compounds selected from the group consisting of organic silicon compounds, organic titanium compounds and organic zirconium compounds are added in the dispersed solution to cause a hydrolysis reaction of the organic metal compound for treating the surface of the inorganic oxide microparticles, and then the inorganic oxide microparticles are dried. Because the inorganic oxide microparticles obtained by this method have been subjected to the surface treatment after calcination, not only the refractive index can be adjusted, but also improvement of the dispersibility in a hardenable resin or adhesion to the resin can be much expected.

[Dental Composite Material]

The dental composite material according to the present invention contains the dental filler and a hardenable resin.

The hardenable resin, which may be used in the present invention, includes, but not limited to, acrylic resin, methacrylic resin, epoxy resin, vinyl resin, and urethane resin. Any of the hardenable resins is selected according to an application of the dental composite material, and sometimes two or more types of hardenable resins may be mixed in use.

Any known method can be employed for producing the dental composite material, but generally the dental composite material can be produced by homogeneously mixing 10 to 50 weight portions of the dental filler, 10 to 50 weight portions of the hardenable resin, and 0.1 to 5 weight portions of a catalyst for polymerization of the hardenable resin or a photo polymerization initiator thereof with agitation. In this case, it is possible to further add a stabilizer, a thickening agent, a coloring agent, a flavor preserving agent, an antibiotic agent, an aromatic substance and/or an auxiliary substance.

The dental composite material produced as described above can advantageously be used in such applications as dental restoratives, dental adhesives, dental mill blanks, dental cements, artificial dentures, dental corrective devices, adhesive agents for dental correction, dental casting, dental coating and the like.

EXAMPLES AND COMPARATIVE EXAMPLES

The present invention is described in detail below with reference to examples and comparative examples. It is to be noted that the present invention is not limited to the examples.
Preparation of the Zirconium Oxide Hydrate

Preparation Example 1

250 Kg of zirconium oxychloride ($ZrOCl_2.8H_2O$, produced by Taiyo Koko Co., Ltd) was added to 4375 Kg of pure water kept at the temperature of 15° C. with agitation to dissolve the zirconium oxychloride therein.

Furthermore, 250 L of ammonia water with the concentration of 15% by weight was slowly dripped with agitation in the aqueous solution of zirconium oxychloride for causing a neutralization reaction of the zirconium oxychloride at 15° C. to obtain a slurry containing a hydrate of zirconium oxide.

Then the slurry was subjected to filtration, and the obtained cake-like substance was washed by pure water repeatedly to remove unreacted materials and byproducts in the neutralization reaction.

As a result, 860 Kg of the cake-like substance was obtained, and the substance contained a hydrate of zirconium oxide at the concentration of 10% by weight and the remaining balance component was water.
Preparation of the Silicic Acid Solution

Preparation Example 2

10 Kg of water glass procurable from the market (Asahi Glass S.I. Tec. Co., Ltd.) was diluted with 38 Kg of pure water, and then was de-alkalized with a cation exchange resin (produced by Mitsubishi Chemicals. CO., Ltd.) to prepare 9 Kg of an aqueous solution of silicic acid. The pH of the aqueous solution was 3 and the concentration of silicon compounds therein was 4% by weight in terms of $SiO_2$.
Preparation of Inorganic Oxide Microparticles

Example 1

2511 g of pure water was added to 289 g of the cake-like substance containing the hydrate of zirconium oxide prepared in Preparation example 1, and then 56 g of a potassium hydroxide reagent containing potassium hydroxide at the purity of 85% by weight (produced by Kanto Chemical Co., Inc.) was added with agitation to the above solution to make the mixture solution alkaline, and 560 g of hydrogen peroxide solution containing hydrogen peroxide at the concentration of 35% by weight (Hayashi Pure Chemical Industry, Ltd.) was further added to the mixture solution.

The resultant mixture solution was agitated for 1 hour to peptize and dissolve the hydrate of zirconium oxide in the aqueous solution. With the operations as described above, 3416 g of aqueous solution containing zirconium components at the concentration of 1% by weight in terms of $ZrO_2$ (this solution is referred to as "example solution 1A" hereinafter) was obtained.

Then, 1512 g of the aqueous solution of silicic acid prepared in Preparation example 2 and 3416 g of the example solution 1A were mixed with each other to obtain 4928 g of an aqueous solution containing zirconium components at the concentration of 24% by weight in terms of $ZrO_2$ and silicon components at the concentration of 65% by weight in terms of $SiO_2$ (the solution is referred to as "example solution 1B" hereinafter).

Then 4928 g of the example solution 1B was put in an autoclave made from stainless steel (produced by Taiatsu Techno Corporation) and was subjected to a hydrothermal treatment for 16 hours at 160° C. With this operation, 4900 g of an aqueous solution was obtained, and the aqueous solution contained solid material substantially comprising oxides or complex oxides of zirconium, silicon and potassium (the solution is referred to as "example solution 1C" hereinafter).

Then, the water content of the example solution 1C was reduced by ultrafiltration until the concentration of the solid material contained therein becomes about 2% by weight, and the solid material was dried for 16 hours at 110° C. in a drying apparatus. With this operation, 50 g of amorphous inorganic oxide microparticles fully dried was obtained. Furthermore, the inorganic oxide microparticles were put in a mortar for pulverizing particles having relatively large diameters or blocks to obtain 48 g of inorganic oxide microparticles having the particle diameters being not widely ranged and with a narrow distribution (the microparticles are referred to as "example microparticles 1A" hereinafter).

Then 48 g of the example microparticles 1A were put in a quartz-made crucible and the crucible was placed in an electric furnace (produced by Toyo Engineering Works Co., Ltd.), and then the example microparticles 1A were calcined for 3 hours at 1000° C. With the operations as described above, 45 g of the inorganic oxide microparticles with a crystalline structure (the microparticles are referred to as "example microparticles 1B" hereinafter) was obtained.

Of the example microparticles 1B obtained as described above, samples of inorganic oxide microparticles were taken out, and were subject to an X-ray diffractometer (RINT-1400, X-ray diffraction method) for measurement of X-ray diffraction peaks. As a result, it was determined that the inorganic oxide microparticles contained a zirconium trisilicate compound with a wadeite type crystalline structure as shown in FIG. 1.

Further, the average particle diameter, density, refractive index, and compression strength of the inorganic oxide microparticles sampled from the example microparticles 1B were measured. The result is as shown in Table 1.

The above measurements were performed as described below.
(a) Average Particle Diameter The inorganic oxide microparticles were added in a water-glycerin solution (the weight ratio of water/glycerin=6/4), so that the content of the microparticles becomes 1% by weight. Then, a cell, in which the above mixture solution was put in, was set in a granulometer based on the centrifugal sedimentation system (produced by Horiba Company: CAPA 700) to measure the average diameter of the inorganic oxide microparticles. The measurement was performed under the conditions with a table's rotating speed of 1000 rpm and the granularity range from 0.5 to 15 µm.

(b) Density 10 g of the inorganic oxide microparticles as a sample and 50 cc of distilled water were put and suspended in a 100 cc flask. Then the flask is vacuumed to substitute gas, which is present in the clearance between the sample particles and also in pores of the particles, with water, and furthermore water was filled up to a reference line of the flask. The measurement was performed in the state.

(c) Refractive Index 0.2 g of the inorganic oxide microparticles as a sample and 0.2 g of the Cargilie standard refractive solution were homogeneously mixed to obtain a paste material. Then, a metallic ring with a thickness of 1 mm was placed on a slide glass plate, the paste material was set into the ring. Then a cover glass sheet was placed thereon and slightly pressed toward the ring. Transparency of the paste material was visually checked.

(d) Compression Strength

A sample of the inorganic oxide microparticles (having particle diameters of 3 to 4 µm) was placed on a diamond platen of a micro compression testing machine (produced by Shimazu Corporation), and a load was given onto the sample for measuring a relation between a load pressure and a compressive displacement to obtain a compression strength of the particles.

Example 2

2152 g of pure water was added to 250 g of the cake-like substance containing a hydrate of zirconium oxide prepared in Preparation example 1, and then 48 g of a potassium hydroxide reagent containing potassium hydroxide at the purity of 85% by weight (produced by Kanto Chemical Co., Inc.) was added with agitation to the above solution to make the mixture solution alkaline, and 480 g of hydrogen peroxide solution containing hydrogen peroxide at the concentration of 35% by weight (produced by Hayashi Pure Chemical Industry, Ltd.) was further added to the mixture solution.

The resultant mixture solution was agitated for 1 hour to peptize and dissolve the hydrate of zirconium oxide in the aqueous solution. With the operations as described above, 2930 g of aqueous solution containing zirconium components at the concentration of 1% by weight in terms of $ZrO_2$ (the solution is referred to as "example solution 2A" hereinafter) was obtained.

Then, 753 g of the aqueous solution of silicic acid prepared in Preparation example 2 and 2930 g of the example solution 2A were mixed with each other to obtain 3683 g of an aqueous solution containing zirconium components at the concentration of 28% by weight in terms of $ZrO_2$ and silicon components at the concentration of 46% by weight in terms of $SiO_2$ (the solution is referred to as "example solution 2B" hereinafter)

Then, 3683 g of the example solution 2B was put in an autoclave made from stainless steel (produced by Taiatsu Techno Corporation) and was subjected to a hydrothermal treatment for 16 hours at 160° C. With this operation, 3603 g of an aqueous solution was obtained, and the aqueous solution contained a solid material substantially comprising oxides or complex oxide of zirconium, silicon and potassium (the solution is referred to as "example solution 2C" hereinafter).

Then, the water content of the example solution 2C was reduced by ultrafiltration until the concentration of the solid material contained therein becomes about 2% by weight, and the solid material was dried for 16 hours at 110° C. in a drying apparatus. With this operation, 50 g of amorphous inorganic oxide microparticles fully dried was obtained. Furthermore, the inorganic oxide microparticles were put in a mortar for pulverizing particles having relatively large diameters or blocks to obtain 48 g of inorganic oxide microparticles having the particle diameters being not widely ranged and with a narrow distribution (the solution is referred to as "example microparticles 2A" hereinafter).

Then 48 g of the example microparticles 2A were put in a quartz-made crucible and the crucible was placed in an electric furnace (produced by Toyo Engineering Works Co., Ltd.), and then the example microparticles 2A were calcined for 3 hours at 1000° C. With the operations as described above, 45 g of the inorganic oxide microparticles with a crystalline structure (the microparticles are referred to as "example microparticles 2B" hereinafter) was obtained.

Of the example microparticles 2B obtained as described above, samples of inorganic oxide microparticles were taken out, and were subject to an X-ray diffractometer (RINT-1400, X-ray diffraction method) for measurement of X-ray diffraction peaks. As a result, it was determined that the inorganic oxide microparticles contained a zirconium trisilicate compound and a zirconium disilicate compound as shown in FIG. 2.

Further, the average particle diameter, density, refractive index, and compression strength of the inorganic oxide microparticles sampled from the example microparticles 2B were measured like in Example 1. The result is as shown in Table 1.

Example 3

1254 g of pure water was added to 145 g of the cake-like substance containing a hydrate of zirconium oxide prepared in Preparation example 1, and then 17 g of a potassium hydroxide reagent containing potassium hydroxide at the purity of 85% by weight (produced by Kanto Chemical Co., Inc.) and 21 g of a sodium hydroxide reagent containing sodium hydroxide at the purity of 48% by weight (produced by Kanto Chemical Co., Inc.) were added with agitation to the above solution to make the mixture solution alkaline, and 280 g of hydrogen peroxide solution containing hydrogen peroxide at the concentration of 35% by weight (produced by Hayashi Pure Chemical Industry, Ltd.) was further added to the mixture solution.

The resultant mixture solution was left with agitation for 1 hour to peptize and dissolve the hydrate of zirconium oxide in the aqueous solution. With the operations as described above, 1400 g of an aqueous solution containing zirconium components at the concentration of 1% by weight in terms of $ZrO_2$ (the solution is referred to as "example solution 3A" hereinafter) was obtained.

Then, 753 g of the aqueous solution of silicic acid prepared in Preparation example 2 and 1400 g of the example solution 3A were mixed with each other to obtain 2153 g of an aqueous solution containing zirconium components at the concentration of 24% by weight in terms of $ZrO_2$ and silicon components at the concentration of 65% by weight in terms of $SiO_2$ (the solution is referred to as "example solution 3B" hereinafter).

Then, 2000 g of the example solution 3B was put in an autoclave made from stainless steel (produced by Taiatsu Techno Corporation) and was subjected to a hydrothermal treatment for 16 hours at 160° C. With this operation, 1950 g of an aqueous solution was obtained, and the aqueous solution contained a solid material substantially comprising oxides or complex oxides of zirconium, silicon and potassium (the solution is referred to as "example solution 3C" hereinafter).

Then, the water content of the example solution 3C was reduced by ultrafiltration until the concentration of the solid material contained therein becomes about 2% by weight, and the solid material was dried for 16 hours at 110° C. in a drying apparatus. With this operation, 40 g of amorphous inorganic oxide microparticles fully dried was obtained. Furthermore, the inorganic oxide microparticles were put in a mortar for pulverizing particles having relatively large diameters or blocks to obtain 38 g of inorganic oxide microparticles having the particle diameters being not widely ranged and with a narrow distribution (the microparticles are referred to as "example microparticles 3A" hereinafter).

Then 38 g of the example microparticles 3A were put in a quartz-made crucible and the crucible was placed in an electric furnace (produced by Toyo Engineering Works Co., Ltd.), and then the example microparticles 3A were calcined for 3 hours at 1000° C. With the operations as described above, 36 g of the inorganic oxide microparticles with a crystalline structure (the micropores are referred to as "example microparticles 3B" hereinafter) was obtained.

Of the example microparticles 3B obtained as described above, sample of inorganic oxide microparticles were taken out, and were subject to an X-ray diffractometer (RINT-1400, X-ray diffraction method) for measurement of X-ray diffraction peaks. As a result, it was determined that the inorganic oxide microparticles contained a zirconium trisilicate compound with the $KNaZrSi_3O_9$ type crystalline structure.

Further, the average particle diameter, density, refractive index, and compression strength of the inorganic oxide microparticles sampled from the example microparticles 3B were measured like in Example 1. The result is as shown in Table 1.

Example 4 and Comparative Example 1

20 Kg of a solution 4B was prepared by the same method as that employed for preparing the example solution 1 B in Example 1.

Then, samples each having the weight of 4928 g were taken from the solution 4B, and the samples were put in autoclaves each made from stainless steel (produced by Taiatsu Techno Corporation), and were subjected to a hydrothermal treatment for 16 hours at 90° C., 110° C., and 200° C. respectively. With the operations as described above, aqueous solutions containing a solid material substantially comprising oxides or complex oxides of zirconium, silicon and potassium were obtained (the solutions are hereinafter referred to as "comparative example solution 1C", "example solution 4C-1", and "example solution 4C-2" respectively).

Then, the water content each of the comparative example solution 1C, the example solution 4C-1 and the example solution 4C-2 was reduced by ultrafiltration until the concentration of a solid material contained in each solution becomes about 2% by weight, and the solid material was dried for 16 hours at 110° C. in a drying apparatus. With the operation, fully dried amorphous inorganic oxide microparticles were obtained. Furthermore, each of the inorganic oxide microparticles was put in a mortar for pulverizing particles having large diameters or blocks to obtain inorganic oxide microparticles having the particle diameters being not widely ranged and with a narrow distribution (the microparticles are hereinafter referred to "comparative example microparticles 1A", "example microparticles 4A-1", and "example microparticles 4A-2" respectively). As a result, weights of the comparative example microparticles 1A, the example microparticles 4A-1, and the example microparticles 4A-2 as described above were 42 g, 44 g, and 41 g respectively.

Then, each of the sample microparticles was calcined under the same conditions as those employed in Example 1 to obtain the inorganic oxide microparticles (the microparticles are hereinafter referred to as "comparative example microparticles 1B", "example microparticles 4B-1", and "example microparticles 4B-2" respectively).

Samples of inorganic oxide microparticles were taken out from the comparative example microparticles 1B, the example microparticles 4B-1, and the example microparticles 4B-2 respectively, and were subjected to an X-ray diffractometer (RINT-1400, X-ray diffraction method) for measurement of X-ray diffraction peaks to check it on whether a zirconium silicate compound exists or not in the particles, like in Example 1. Furthermore, the average particle diameter, density, refractive index, and compression strength of the inorganic oxide microparticles sampled from the comparative example microparticles 1B, the example microparticles 4B-1, and the example microparticles 4B-2 were measured like in Example 1. The result is as shown in Table 1.

Example 5 and Comparative Example 2

20 Kg of a solution 5B was prepared by the same method as that employed for preparing the example solution 1B in Example 1.

Then, samples each having the weight of 4928 g were taken from the solution 5B, and the samples were put in autoclaves each made from stainless steel (produced by Taiatsu Techno Corporation), and were subjected to a hydrothermal treatment for 96 hours at 90° C., 110° C., and 200° C. respectively. With the operations as described above, aqueous solution containing a solid material substantially comprising oxides or complex oxides of zirconium, silicon and potassium were obtained (the solutions are hereinafter referred to as "comparative example solution 2C", "example solution 5C-1", and "example solution 5C-2" respectively).

Then, the water content each of the comparative example solution 2C, the example solution 5C-1 and the example solution 5C-2 was reduced by ultrafiltration until the concentration of a solid material contained in each solution becomes about 2% by weight, and the solid material was dried for 16 hours at 110° C. in a drying apparatus. With the operation, fully dried amorphous inorganic oxide microparticles were obtained. Furthermore, each of the inorganic oxide microparticles was put in a mortar for pulverizing particles having large diameters or blocks to obtain inorganic oxide microparticles having the particle diameters being not widely ranged and with a narrow distribution (the microparticles are hereinafter referred to "comparative example microparticles 2A", "example microparticles 5A-1", and "example microparticles 5A-2" respectively). As a result, weights of the comparative example microparticles 2A, the example microparticles 5A-1, and the example microparticles 5A-2 as described above were 42 g, 44 g, and 41 g respectively.

Then, each of the sample microparticles was calcined under the same conditions as those employed in Example 1 to obtain the inorganic oxide microparticles (the microparticles are hereinafter referred to as "comparative example microparticles 2B", "example microparticles 5B-1", and "example microparticles 5B-2" respectively).

Samples of inorganic oxide microparticles were taken out from the comparative example microparticles 2B, the example microparticles 5B-1, and the example microparticles 5B-2 respectively, and were subjected to an X-ray diffractometer (RINT-1400, X-ray diffraction method) for measurement of X-ray diffraction peaks to check it on whether a zirconium silicate compound exists or not in the particles, like in Example 1. Furthermore, the average particle diameter, density, refractive index, and compression strength of the inorganic oxide microparticles sampled from the comparative example microparticles 2B, the example microparticles 5B-1 and the example microparticles 5B-2 were measured like in Example 1. The result is as shown in Table 1.

Example 6 and Comparative Example 3

120 g of microparticles 6A were prepared by the same method as that employed for preparing the example microparticles 1A in Example 1.

Then, samples each having the weight of 30 g were taken from the microparticles 6A, and put in quartz-made crucibles, and each of the crucibles was further placed in a electric furnace (produced by Toyo Engineering Works Co., Ltd.). Then, each of the inorganic oxide microparticles placed in the crucibles was calcined for 3 hours at 700° C., 900° C., and 1100° C. respectively. With the operations as described above, the samples of the inorganic oxide microparticles calcined were obtained (the microparticles are hereinafter referred to as "comparative example microparticles 3B", "example microparticles 6B-1", and "example microparticles 6B-2" respectively).

Samples of inorganic oxide microparticles were taken out from the comparative example microparticles 3B, the example microparticles 6B-1, and the example microparticles 6B-2 respectively, and were subjected to an X-ray diffractometer (RINT-0.1400, X-ray diffraction method) for measurement of X-ray diffraction peaks to check it on whether a zirconium silicate compound exists or not in the particles, like in Example 1. Furthermore, the average particle diameter, density, refractive index, and compression strength of the inorganic oxide microparticles sampled from the comparative example microparticles 3B, the example microparticles 6B-1, and the example microparticles 6B-2 were measured like in Example 1. The result is as shown in Table 1.

Example 7

3000 g of a solution 7C was prepared by the same method as that employed for preparing the example solution 1C in Example 1.

A concentration of a solid material contained in the solution 7C was adjusted to 2% by weight with use of ultrafiltration, and then the solution was subjected to a spray drier (Niro Atomizer). The spray drier was operated for spray-drying the solid material contained in the solution, under the conditions that the solution is introduced in the drier with the supply rate of 2 L/min and the supply pressure of 0.5 MPa, and is sprayed from a nozzle in a hot air stream having a temperature of 180° C. With the operation, the fully dried example microparticles 7A were obtained. 50 g of the obtained example microparticles 7A was fully mixed with 100 g of ethanol in a 250 cc beaker (height: 105 mm), and the mixture was left for 1 hour. Then, a solution at the depth of about 3 cm from the liquid level (i.e., the surface of the supernatant liquid), a solution in the range from about 3 to 6 cm from the liquid level, a solution in the range from about 6 to 9 cm from the liquid level, and a solution at the depth of about 9 cm from the liquid level or below were sampled (the solutions are hereinafter referred to as "example solution 7C-1", "example solution 7C-2", "example solution 7C-3" and "example solution 7C-4" respectively).

The example solution 7C-1, the example solution 7C-2, the example solution 7C-3, and the example solution 7C-4 were dried for 16 hours at 110° C. in a drying apparatus. As a result, each of the fully dried inorganic oxide microparticles were obtained (the microparticles are hereinafter referred to "example microparticles 7A-1", "example microparticles 7A-2", "example microparticles 7A-3" and "example microparticles 7A-4" respectively), and weights of the example microparticles 7A-1, the example microparticles 7A-2, the example microparticles 7A-3, and the example microparticles 7A-4 were 10 g, 10 g, 10 g, and 10 g respectively.

Then, each of the above microparticles was calcined under the same conditions as those employed in Example 1 to obtain the inorganic oxide microparticles for the samples (the microparticles are hereinafter referred to "example microparticles 7B-1", "example microparticles 7B-2", "example microparticles 7B-3", and "example microparticles 7B-4" respectively).

Samples of inorganic oxide microparticles were taken out from the example microparticles 7B-1, and the example microparticles 7B-2, the example microparticles 7B-3, and the example microparticles 7B-4 respectively, and were subjected to an X-ray diffractometer (RINT-1400, X-ray diffraction method) for measurement of X-ray diffraction peaks to check it on whether a zirconium silicate compound exists or not in the particles, like in Example 1. Furthermore, the average particle diameter, density, refractive index, and compression strength of the inorganic oxide microparticles sampled, from the example microparticles 7B-1, and the example microparticles 7B-2, the example microparticles 7B-3, and the example microparticles 7B-4 were measured like in Example 1. The result is as shown in Table 1.

Example 8 and Comparative Example 4

20 Kg of a solution 8A was prepared by the same method as that employed for preparing the example solution 1A in Example 1.

Then the aqueous silicic acid solution prepared in Preparation example 2 and the solution 8A were mixed with each other at the molar ratios ($SiO_2/ZrO_2$) as shown below. In the molar ratios, silicon components contained in the aqueous silicic acid solution are expressed as $SiO_2$ (i.e., in terms of $SiO_2$) and zirconium components contained in the solution 8A are expressed as $ZrO_2$ (i.e., in terms of $ZrO_2$).

|  | Silicic acid solution (g) | Solution 8A (g) | Molar ratio ($SiO_2/ZrO_2$) |
| --- | --- | --- | --- |
| Mixed solution 1 | 2010 | 1003 | 80/5 |
| Mixed solution 2 | 505 | 2201 | 20/11 |
| Mixed solution 3 | 1508 | 3043 | 60/15 |
| Mixed solution 4 | 1022 | 3234 | 40/32 |

Then, samples each having the weight of 2000 g were taken from the mixture solutions 1 to 4 (namely, the comparative example solutions 4B-1, example solution 8B-1, example solution 8B-2, and comparative example solution 4B-2), and the samples were put in autoclaves each made from stainless steel (produced by Taiatsu Glass Corporation), and were subjected to a hydrothermal treatment for 16 hours at 160° C. With this operation as described above, aqueous solutions containing solid material substantially comprising oxides or complex oxides of zirconium, silicon and potassium (the solutions are hereinafter referred to as "comparative example solution 4C-1", "example solution 8C-1", "example solution 8C-2", and "comparative example solution 4C-2" respectively) were obtained.

Then, the water content each of the comparative example solution 4C-1, the example solution 8C-1, the example solution 8C-2, and the comparative example solution 4C-2 were reduced by ultrafiltration until a concentration of a solid material contained in each solution becomes about 2% by weight, and the solid material was dried for 16 hours at 110° C. in a drying apparatus. With the operation above, fully dried amorphous inorganic oxide microparticles were obtained. Furthermore, each of the inorganic oxide microparticles was put in a mortar for pulverization of particles having large diameters of blocks to obtain inorganic oxide microparticles having the particle diameters being not widely ranged and with a narrow distribution (the microparticles are hereinafter referred to "comparative example microparticles 4A-1", "example microparticles 8A-1", "example microparticles 8A-2" and "comparative example microparticles 4A-2" respectively). As a result, weights of the comparative example microparticles 4A-1, the example microparticles 8A-1, the example microparticles 8A-2 and the comparative example microparticles 4A-2 as described above were 21 g, 19 g, 18 g and 17 g respectively.

Then, each of the sample microparticles was calcined under the same conditions as those employed in Example 1 to obtain inorganic oxide microparticles (the microparticles are hereinafter referred to as comparative example microparticles 4B-1, example microparticles 8B-1, example microparticles 8B-2, and comparative example microparticles 4B-2 respectively).

Samples of inorganic oxide microparticles were taken out from the comparative example microparticles 4B-1, the example microparticles 8B-1, the example microparticles 8B-2, and the comparative example microparticles 4B-2 respectively, and were subjected to an X-ray diffractometer (RINT-1400, X-ray diffraction method) for measurement of X-ray diffraction peaks to check it on whether a zirconium silicate compound exists or not in the particles, like in Example 1. Furthermore, the average particle diameter, density, refractive index, and compression strength of the inorganic oxide microparticles sampled from the comparative example microparticles 4B-1, the example microparticles 8B-1, the example microparticles 8B-2, and the comparative example microparticles 4B-2 were measured like in Example 1. The result is as shown in Table 1.

Example 9

120 g of microparticles 9B were prepared by the same method as that employed for preparing the example microparticles 1B in Example 1.

Then, 100 g of the microparticles were taken out from the microparticles 9B and were put in a glass vessel, and 18 g of ethanol reagent containing ethyl alcohol at 99.5% by weight and water at 0.5% by weight, and 12 g of γ-methacryloxypropyltrimethoxysilane were further added into the vessel. For the surface treatment of the sample, the mixture was sufficiently mixed with agitation for 1 hour, and then was dried in a drying apparatus for 16 hours at 110° C. With the operation, the surface of the microparticles 9B was treated with hydrolysate of the γ-methacryloxypropyltrimethoxysilane, and 112 g of the example microparticles 9BX was obtained.

A sample of inorganic oxide microparticles was taken out from the example microparticles 9BX obtained as described above, and was subjected to an X-ray diffractometer (RINT-1400, X-ray diffraction method) for measurement of X-ray diffraction peaks to check it on whether a zirconium silicate compound exists or not in the particles, like in Example 1. Furthermore, the average particle diameter, density, refractive index, and compression strength of the inorganic oxide microparticles sampled from the example microparticles 9BX were measures like in Example 1. The result is as shown in Table 1.

Example 10

120 g of microparticles 10B was prepared by the same method as that employed for preparing the example microparticles 5B-2 in Example 5.

Then, a sample having the weight of 100 g was taken out from the microparticles 10B and was put in a glass vessel, and 18 g of ethanol containing ethyl alcohol at 99.5% by weight and water at 0.5% by weight and 12 g of γ-methacryloxypropyltrimethoxysilane were added in the vessel. For surface treatment of the sample, the mixture was sufficiently mixed with agitation for 1 hour, and then was dried in a drying apparatus for 16 hours at 110° C. With the operation, the surface of the microparticles 10B was treated with hydrolysate of the γ-methacryloxypropyltrimethoxysilane, and 112 g of the example microparticles 10BX was obtained.

A sample of inorganic oxide microparticles was taken out from the example microparticles 10BX obtained as described above, and was subjected to an X-ray diffractometer (RINT-1400, X-ray diffraction method) for measurement of X-ray diffraction peaks to check it on whether a zirconium silicate compound exists or not in the particles, like in Example 1. Furthermore, the average particle diameter, density, refractive index, and compression strength of the inorganic oxide microparticles sampled from the example microparticles 10BX were measured like in Example 1. The result is as shown in Table 1.

Comparative Example 5

120 g of microparticles 5B was prepared by the same method as that employed for preparing the comparative example microparticles 3B in Example 3.

Then, a sample having the weight of 100 g was taken out from the microparticles 5B and was put in a glass vessel, and 18 g of ethanol containing ethyl alcohol at 99.5% by weight and water at 0.5% by weight and 12 g of γ-methacryloxypropyltrimethoxysilane were added in the vessel. For the surface treatment of the sample, the mixture was sufficiently mixed with agitation for 1 hour, and then was dried in a drying apparatus for 16 hours at 110° C. With the operation, the surface of the microparticles 5B was treated with hydrolysate of the γ-methacryloxypropyltrimethoxysilane, and 112 g of the comparative example microparticles 5BX was obtained.

A sample of inorganic oxide microparticles was taken out from the comparative example microparticles 5BX, and was subjected to an X-ray diffractometer (RINT-1400, X-ray diffraction method) for measurement of X-ray diffraction peaks to check it on whether a zirconium silicate compound exists or not in the particles, like in Example 1. Furthermore, the average particle diameter, density, refractive index, and compression strength of the inorganic oxide microparticles sampled from the comparative example microparticles 5BX were measured like in Example 1. The result is as shown in Table 1.

Comparative Example 6

100 g of silica microparticles having the average particle diameter of 6 μm (produced by Catalysts & Chemicals Industries Co., Ltd.: Silica microbead p-1500) was put in a glass vessel, and 18 g of ethanol containing ethyl alcohol at 99.5% by weight and water at 0.5% by weight and 12 g of γ-methacryloxypropyl trimethoxysilane were added in the vessel. For surface treatment of the sample, the mixture was sufficiently mixed with agitation for 1 hour, and then was dried in a drying apparatus for 16 hours at 110° C. With the operation, the surface of the microparticles 6B was treated with hydrolysate of the γ-methacryloxypropyl trimethoxysilane, and 112 g of the comparative example microparticles 6BX was obtained.

A sample of inorganic oxide microparticles was taken out from the comparative example microparticles 6BX obtained as described above, and was subjected to an X-ray diffractometer (RINT-1400, X-ray diffraction method) for measurement of X-ray diffraction peaks to check it on whether a zirconium silicate compound exists or not in the particles, like in Example 1. Furthermore, the average particle diameter, density, refractive index, and compression strength of the inorganic oxide microparticles sampled from the comparative example microparticles 6BX were measured like in Example 1. The result is as shown in Table 1.

Comparative Example 7

A silica sol containing silica particles having the average particle diameter of 17 nm at the concentration of 10% by weight in terms of $SiO_2$ (produced by Catalysts & Chemicals Industries Co., Ltd.: Cataloid S-20L) was diluted with distilled water to obtain 1867 g of silica sol containing silica particles by 3% by weight. Then, 12 g of aqueous NaOH solution containing NaOH at the concentration of 3% by weight and 407 g of an aqueous solution of ammonium zirconyl carbonate containing zirconium components at the concentration of 4% by weight in terms of $ZrO_2$ (the reagent was produced by Daiichi Kigenso Kagaku Kogyo Co., Ltd.: Zircosole AC-7), and the mixture was agitated for 15 minutes to obtain 2286 g of a slurry of the mixture solution.

Then, the mixture solution was subjected to a spray drier (Niro Atomizer). The spray drier was operated for spray-drying a solid material contained in the solution, under the conditions that the solution is introduced in the drier with the supply rate of 2 L/min and the supply pressure of 0.5 MPa, and is sprayed from a nozzle in a hot air stream having a temperature of 180° C. With the operation, fully dried comparative example microparticles 7A were obtained. The obtained comparative example microparticles 7A were calcined for 3 hours at 650° C. With this operation, the comparative example microparticles 7B were obtained.

A sample of inorganic oxide microparticles was taken out from the comparative example microparticles 7B as described above, and was subjected to an X-ray diffractometer (RINT-1400, X-ray diffraction method) for measurement of X-ray diffraction peaks to check it on whether a zirconium silicate compound exists or not in the particles, like in Example 1. Furthermore, the average particle diameter, density, refractive index, and compression strength of the inorganic oxide microparticles sampled from the comparative example microparticles 7B were measured like in Example 1. The result is as shown in Table 1.

Comparative Example 8

120 g of microparticles 8A was prepared by the same method as that employed for preparing the comparative example microparticles 7B in Comparative example 7.

Then, a sample having the weight of 100 g was taken out from the microparticles 8A and was put in a glass vessel, and 18 g of ethanol containing ethyl alcohol at 99.5% by weight and water at 0.5% by weight and 12 g of γ-methacryloxypropyl trimethoxysilane were further added in the vessel. For surface treatment of the sample, the mixture was sufficiently mixed with agitation for 1 hour, and then was dried in a drying apparatus for 16 hours at 110° C. With the operation, the surface of the microparticles 8B was treated with hydrolysate of the γ-methacryloxypropyltrimethoxysilane, and 112 g of the comparative example microparticles 8BX was obtained.

A sample of inorganic oxide microparticles was taken out from the comparative example microparticles 8BX obtained as described above, and was subjected to an X-ray diffractometer (RINT-1400, X-ray diffraction method) for measurement of X-ray diffraction peaks to check it on whether a zirconium silicate compound exists or not in the particles, like in Example 1. Furthermore, the average particle diameter, density, refractive index, and compression strength of the inorganic oxide microparticles sampled from the comparative example microparticles 8BX were measured like in Example 1. The result is as shown in Table 1.

TABLE 1

| Example microparticles No. | Comparative example microparticles No. | Presence of zirconium silicate compound | Average particle diameter (μm) | Density (g/ml) | Refractive index | Compression strength (kgf/cm$^2$) |
|---|---|---|---|---|---|---|
| 1B | | ⊚ | 3.6 | 2.9 | 1.58 | 66 |
| 2B | | ○ | 3.3 | 3.2 | 1.60 | 55 |
| 3B | | ⊚ | 3.2 | 2.9 | 1.58 | 59 |
| 4B-1 | | ⊚ | 3.1 | 2.9 | 1.58 | 65 |
| 4B-2 | | ⊚ | 2.9 | 2.8 | 1.58 | 63 |
| 5B-1 | | ⊚ | 2.2 | 2.9 | 1.58 | 68 |
| 5B-2 | | ⊚ | 2.8 | 2.9 | 1.58 | 80 |
| 6B-1 | | ⊚ | 3.1 | 3.0 | 1.58 | 60 |
| 6B-2 | | ⊚ | 3.0 | 2.9 | 1.58 | 65 |
| 7B-1 | | ⊚ | 1.2 | 2.9 | 1.58 | 58 |
| 7B-2 | | ⊚ | 2.1 | 3.0 | 1.58 | 64 |
| 7B-3 | | ⊚ | 3.1 | 2.9 | 1.58 | 70 |
| 7B-4 | | ⊚ | 9.0 | 2.9 | 1.58 | 60 |

TABLE 1-continued

| Example microparticles No. | Comparative example microparticles No. | Presence of zirconium silicate compound | Average particle diameter (μm) | Density (g/ml) | Refractive index | Compression strength (kgf/cm²) |
|---|---|---|---|---|---|---|
| 8B-1 |  | Δ | 3.4 | 3.3 | 1.61 | 54 |
| 8B-2 |  | ○ | 3.6 | 3.2 | 1.60 | 52 |
| 9BX |  | ⊚ | 3.3 | 2.8 | 1.57 | 66 |
| 10BX |  | ⊚ | 2.8 | 2.8 | 1.57 | 79 |
|  | 1B | X | 2.9 | 2.9 | 1.53 | 35 |
|  | 2B | X | 2.7 | 2.9 | 1.53 | 33 |
|  | 3B | X | 2.9 | 2.9 | 1.53 | 37 |
|  | 4B-1 | X | 2.6 | 2.7 | 1.49 | 28 |
|  | 4B-2 | X | 3.2 | 3.5 | 1.61 | 55 |
|  | 5BX | X | 2.9 | 2.9 | 1.53 | 35 |
|  | 6BX | X | 5.6 | 2.2 | 1.45 | 14 |
|  | 7B | X | 3.0 | 2.9 | 1.51 | 34 |
|  | 8BX | X | 3.0 | 2.8 | 1.50 | 35 |

Note
In Table 1 above, ⊚ indicates that a zirconium trisilicate compound is mainly contained in the inorganic oxide microparticles (i.e., the calcined particles B), ○ indicates that a zirconium trisilicate compound and a zirconium disilicate compound are contained in the inorganic oxide microparticles (i.e., the calcined particles B), Δ indicates that zirconium disilicate compound is mainly contained in the inorganic oxide microparticles (i.e., the calcined particles B), and X indicates that a zirconium silicate compound is little contained in the inorganic oxide microparticles (i.e., the calcined particles B).

Preparation of Dental Composite Material

Example 11 and Comparative Example 9

130 g of urethanedimethacrylate and 70 g of triethyleneglycol dimethacrylate were mixed with each other, and 2 g of camphorquinone and 4 g of dimethylaminoethylmethacrylate were added to the mixture for dissolving the mixture to obtain a polymeric monomer.

Samples each having the weight of 30 g were taken out from the polymeric monomer, and then 70 g of the example microparticles 1B, the example microparticles 9BX, the example microparticles 10BX, the comparative example microparticles 5BX, the comparative example microparticles 6BX, and the comparative example microparticles 8BX was added to the samples respectively, and each of the mixtures was sufficiently mixed with agitation for 1 hour to obtain the example paste 11BY-1, the example paste 11BY-2, the example paste 11BY-3, the comparative example paste 9BY-1, the comparative example paste 9BY-2, and the comparative example paste 9BY-3, the weight of which is 100 g respectively.

Then the samples were homogeneously filled in Teflon™-made molds and a light beam was irradiated to the samples to obtain the example composite material 11BZ-1, the example composite material 11BZ-2, the example composite material 11BZ-3, the comparative example composite material 9BZ-1, the comparative example composite material 9BZ-2, and the comparative example composite material 9BZ-3.

Furthermore, measurement was made for the X-ray radiopacity, transparency, and a bending strength of each of the example composite material 11BZ-1, the example composite material 11BZ-2, the example composite material 11BZ-3, the comparative example composite material 9BZ-1, the comparative example composite material 9BZ-2, and the comparative example composite material 9BZ-3. The result is shown in Table 2.

The measurements were performed as described below.
(a) X-Ray Radiopacity

The composite materials were photographed on dental X-ray films with an X-ray imaging equipment. Furthermore, an aluminum plate having a prespecified thickness was photographed simultaneously, and the X-ray radiopacity of the composite material was regarded as 100% when the value was the same as that of the aluminum plate.
(b) Transparency Each of the composite materials was placed on a transparency testing paper sheet divided to white and black portions so that a half of the plate was on the black portion, and the transparency of the plate was observed on both the white and black portions. The evaluation was made on the following criteria.

○: White turbidity or reflected light was not observed, and no coloring was observed in the white portion. (This result means that the transparency is high.)

Δ: The black portion was a little whitened, and slight coloring was observed in the white portion. (This result means that the transparency is slightly low.)

X: The black portion was a little whitened and reflected light was observed, and light-brown color was observed in the write portion. (This result means that the transparency is low.)
(c) Bending Strength Each of the composite materials was preserved in distilled water at 37° C. for 24 hours, and the sample was taken out from the distilled water, and was subjected to a bending strength testing with the Instron Versatile Testing Machine under the conditions including the inter-fulcrum distance of 20 mm, and the cross head speed of 1 mm/minute. Five tested pieces (having a shape of a rectangular parallelepiped with the width of about 2 mm, the height of about 2 mm, and the length of about 25 mm) were prepared for each sample, and the average value was regarded as a bending strength of the sample.

TABLE 2

| Example microparticles No. | Comparative example microparticles No. | X-ray radiopacity (%) | Transparency | Bending strength (kgf/cm²) |
|---|---|---|---|---|
| 11BZ-1 |  | 190 | ○ | 1730 |
| 11BZ-2 |  | 187 | ○ | 1890 |
| 11BZ-3 |  | 185 | ○ | 1680 |
|  | 9BZ-1 | 110 | Δ | 1120 |
|  | 9BZ-2 | 25 or below | X | 714 |
|  | 9BZ-3 | 125 | ○ | 1154 |

Figure 1:
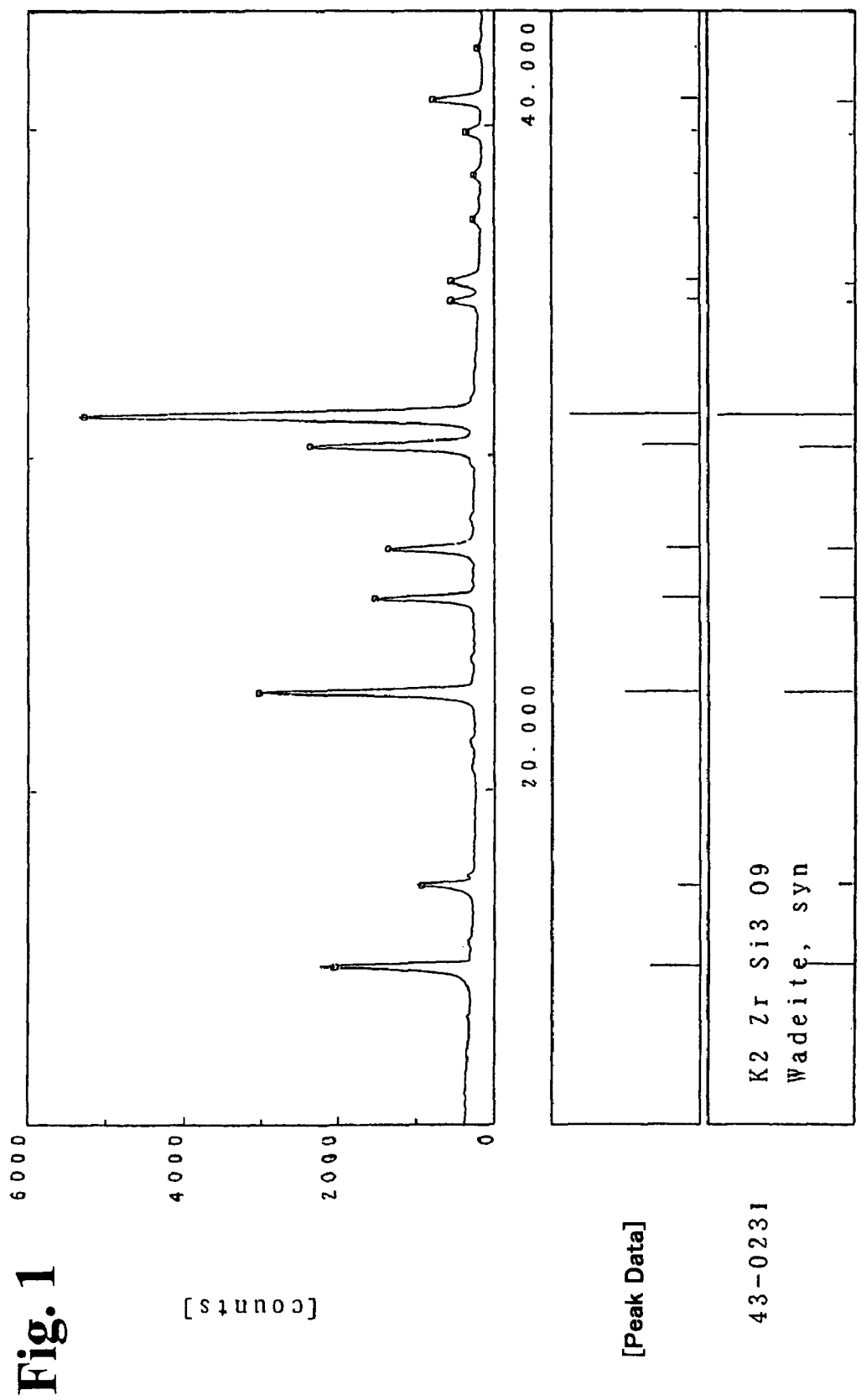
FIG. 1 shows a result of X-ray diffraction testing for the inorganic oxide microparticles containing a zirconium trisilicate compound with a wadeite type crystalline structure (i.e., the example microparticles 1B) prepared in Example 1.
Figure 2:
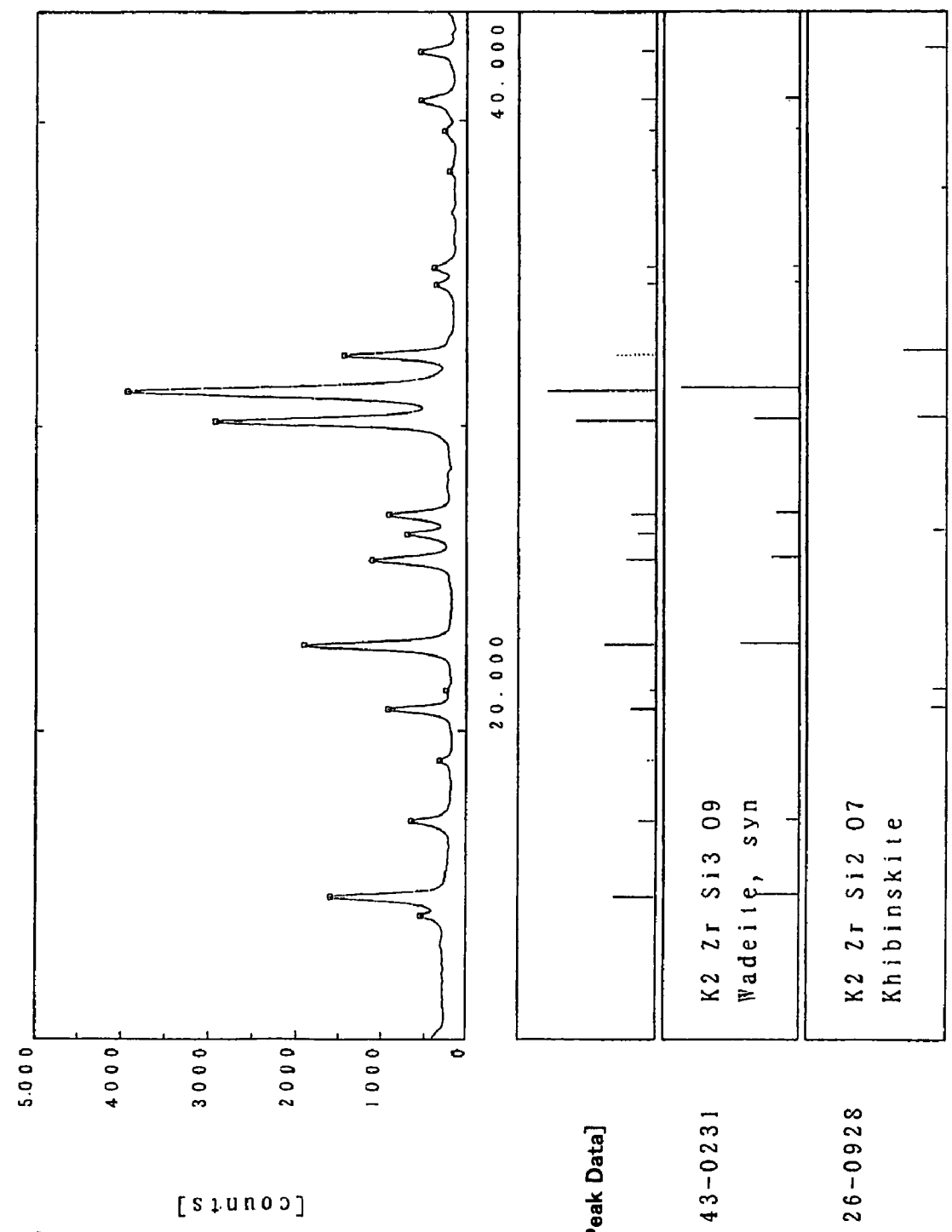
FIG. 2 shows a result of X-ray diffraction testing for the inorganic oxide microparticles containing a zirconium trisilicate compound and a zirconium disilicate compound (I.e., the example microparticles 2B) prepared in Example 2.

The invention claimed is:

1. A dental filler comprising inorganic oxide microparticles having an average particle diameter in a range from 2 nm to 50000 nm, wherein the inorganic oxide microparticles are made from a crystallized zirconium silicate compound selected from the group consisting of zirconium trisilicate, as expressed by the chemical formula $M_2ZrSi_3O_9$ or $M_2ZrSi_3O_9 \cdot H_2O$ (wherein M is an alkali metal), zirconium disilicate, as expressed by the chemical formula $M_2ZrSi_2O_7$ or $M_2ZrSi_2O_7 \cdot H_2O$ (wherein M is an alkali metal), and a mixture thereof.

2. The dental filler according to claim 1, wherein the zirconium trisilicate has a wadeite type crystalline structure.

3. The dental filler according to claim 1, wherein the inorganic oxide microparticles are subjected to surface treatment with at least one organic metal compound selected from the group consisting of organic silicon compounds, organic titanium compounds, and organic zirconium compounds.

4. The dental filler according to claim 1, wherein the dental filler has a refractive index in a range from 1.43 to 1.65.

* * * * *

UNITED STATES PATENT AND TRADEMARK OFFICE
CERTIFICATE OF CORRECTION

| | | |
|---|---|---|
| PATENT NO. | : 8,182,860 B2 | Page 1 of 1 |
| APPLICATION NO. | : 12/225594 | |
| DATED | : May 22, 2012 | |
| INVENTOR(S) | : Ohtsuka et al. | |

It is certified that error appears in the above-identified patent and that said Letters Patent is hereby corrected as shown below:

On the Title Page

Item (22) PCT Filed: Change "Mar. 23, 2007" to --Feb. 23, 2007--.

Signed and Sealed this
Twenty-fourth Day of July, 2012

David J. Kappos
*Director of the United States Patent and Trademark Office*